(12) United States Patent
Lihme

(10) Patent No.: US 8,815,551 B2
(45) Date of Patent: Aug. 26, 2014

(54) PRODUCTION OF BIOFUEL AND PROTEIN FROM A RAW MATERIAL

(75) Inventor: Allan Otto Fog Lihme, Birkerød (DK)

(73) Assignee: Upfront Chromatography A/S, Copenhagen Ø (DK)

( * ) Notice: Subject to any disclaimer, the term of this patent is extended or adjusted under 35 U.S.C. 154(b) by 606 days.

(21) Appl. No.: 12/522,885

(22) PCT Filed: Jan. 15, 2008

(86) PCT No.: PCT/DK2008/050007
§ 371 (c)(1),
(2), (4) Date: Dec. 15, 2009

(87) PCT Pub. No.: WO2008/086811
PCT Pub. Date: Jul. 24, 2008

(65) Prior Publication Data
US 2010/0120107 A1    May 13, 2010

Related U.S. Application Data

(60) Provisional application No. 60/884,948, filed on Jan. 15, 2007.

(51) Int. Cl.
*C12P 7/16* (2006.01)
*A23J 1/00* (2006.01)

(52) U.S. Cl.
USPC ......................................... 435/160; 530/412

(58) Field of Classification Search
None
See application file for complete search history.

(56) References Cited

U.S. PATENT DOCUMENTS

| | | | | |
|---|---|---|---|---|
| 4,326,036 A * | 4/1982 | Hayes | ............................ | 435/161 |
| 6,498,236 B1 * | 12/2002 | Lihme et al. | ................ | 530/387.1 |
| 6,617,133 B1 | 9/2003 | Noda et al. | | |
| 6,620,326 B1 * | 9/2003 | Lihme et al. | ................... | 210/635 |
| 6,783,962 B1 * | 8/2004 | Olander et al. | .............. | 435/91.1 |
| 7,368,141 B2 * | 5/2008 | Lihme | ........................... | 426/531 |
| 7,812,138 B2 * | 10/2010 | Lihme et al. | ................... | 530/412 |
| 2003/0232109 A1 | 12/2003 | Dawley et al. | | |
| 2005/0065329 A1 * | 3/2005 | Lihme et al. | ................... | 530/417 |

FOREIGN PATENT DOCUMENTS

| | | |
|---|---|---|
| EP | 0 147 198 A2 | 7/1985 |
| JP | 61-282097 A | 12/1986 |
| JP | 09-187274 A | 7/1997 |
| JP | 2000-512143 A | 9/2000 |
| JP | 2001-139600 A | 5/2001 |
| JP | 2005-034875 A | 12/2005 |
| RU | 2044770 C1 | 9/1995 |
| WO | WO 92/00799 | 1/1992 |
| WO | WO 92/18237 | 10/1992 |
| WO | WO-97/47650 A1 | 12/1997 |
| WO | WO 02/05922 A1 | 1/2002 |
| WO | WO/02/096215 * | 12/2002 ................ A23J 1/20 |
| WO | WO 03/063606 A1 | 8/2003 |
| WO | WO 2004/082397 A1 | 9/2004 |
| WO | WO 2005/121165 A1 | 12/2005 |
| WO | WO 2006/115422 A1 | 11/2006 |
| WO | WO 2006/119206 A2 | 11/2006 |

OTHER PUBLICATIONS

Willoughby et al., Extreme Scale-Down of Expanded Bed Adsorption: Purification of an Antibody Fragment Directly from Recobmiannt *E. coli* Culture., Biotechnology and Bioengineering., (2004) vol. 87, pp. 641-647.*
Olander et al., Fractionation of high-value whey proteins., Scandinavian Dairy Information, 2001, No. 2., pp. 22-25.*
Pharmacia Handbook (Introduction to Expanded Bed Adsorption, 1997).*
Xu et al., Fats and Oils from Plant Materials, Edited by George Liadakis and Constantina Tzia, CRC Press 2003, Chapter 6, total 35 pages.*
Wu et al., Utilization of Protein-Rich Ethanol co-Products from Corn in Tilapia Feed., JAOCS, vol. 71, pp. 1041-1043.*
Donald Klass, Biomass for Renewable Energy and Fuels, Encyclopedia of Energy (2004), vol. 1, pp. 193-212.*
Affinity Chromatography Amersham Biosciences (2002).*
Hermann Heipieper, Adaptation of *Escherichia coli* to Ethanol on the Level of Membrane Fatty Acid Composition., Appl. Environ. Microbiol. 2005, vol. 71, p. 3388.*
Naccarato et al., Characterization and metabolism of free fatty alcohols from *Escherichia coli*., Lipids, May 1972, vol. 7, Issue 5, pp. 275-281.*
Shah et al., Enzymatic transesterification for biodiesel production., Indian Journal of Biochemistry & Biophysics, (2003), vol. 40, pp. 392-399.*
The Alcohol Textbook (A reference for the beverage, fuel and industrial alcohol industries, 2003, 4th Edition, Edited by KA Jacques, TP Lyons and DR Kelsall, total 448 pages.*
Hennico et al., Esterfip, A transesterification Process to produce bio-diesel from renewable energy sources, (1995), American Chemical Society Division of Fuel Chemistry, vol. 40, pp. 763-767.*
Demetri Petrides, Bioprocess Design and Economics, Bioseparations Science and Engineering, Oxford University Press, 2003, pp. 1-60.*
International Search Report PCT/DK2008/050007 dated May 2, 2008.
Iowa State University, "2003-2004 Annual Report" [Online] 2004, XP002462663, Office of Biorenewables Programs, Ames, IOWA, USA, pp. 1-23.
JP Application No. 2009-545065, Office Action Summary mailed Feb. 5, 2013.
RU Application No. 2009131029/10, Notice of Allowance received Dec. 14, 2012.

* cited by examiner

*Primary Examiner* — Alexander Kim
(74) *Attorney, Agent, or Firm* — Foley & Lardner LLP

(57) ABSTRACT

The present invention relates to a method for providing an isolated biofuel and a purified protein product from a raw material suitable for the production of the biofuel or a derivative of said raw material. The method comprises the steps of: (i) subjecting the raw material or a derivative of said raw material to at least one first treatment liberating the biofuel from the raw material or the derivative of said raw material, (ii) isolating the biofuel liberated in step (i) obtaining the isolated biofuel, (iii) subjecting the raw material or a derivative of said raw material to at least one second treatment providing a material suspension, and (iv) subjecting the material suspension from step (iii) to an expanded bed adsorption process obtaining the purified protein product.

14 Claims, No Drawings

PRODUCTION OF BIOFUEL AND PROTEIN FROM A RAW MATERIAL

CROSS-REFERENCE TO RELATED PATENT APPLICATIONS

This application is the U.S. National Phase of PCT/DK2008/050007 filed Jan. 15, 2008, which claims priority to U.S. Provisional Patent Application No. 60/884,948 filed Jan. 15, 2007, each of which is incorporated herein by reference in it's entirety.

TECHNICAL FIELD OF THE INVENTION

The present invention relates to a method and a system for providing an isolated biofuel and a purified protein product from a raw material. In particular the present invention relates to the combined production of a biofuel and the purification of a protein product using an expanded bed adsorption process from a raw material.

BACKGROUND OF THE INVENTION

Biofuel can be used both for central- and decentralized production of electricity and heat or as petrol replacement.

In one way biofuel is conserved by "capturing" energy from the sun through the process of photosynthesis in growing plants. However, generally, one advantage of biofuel in comparison to most other fuel types is that biofuel is biodegradable, and thus relatively harmless to the environment if spilled.

Biofuel was used in the early days of the car industry. In Germany the combustion engine was provided to run on ethanol and the diesel engine was initially made to run on peanut oil. However due to very cheap extraction of crude oil (crude mineral oil) the industry preferred to provide engines running on the cheaper extracts of crude mineral oils rather the more expensive biofuels.

Nevertheless, biofuel remained a slightly interesting combusting ingredient in particular in a blend with petrol or as a blend of gasoline with alcohol fermented from potatoes in some countries, such as Germany and Britain.

However, due to the increasing use of combustible fuels and at the same time avoid or limit the stress on the surrounding environment, alternative fuel-products which are relatively harmless to the environment, such as biofuels, have gained more attention. Hence, as of 2005, bioenergy, such as biofuel, covers approximately 15% of the world's energy consumption and the consumption is still increasing.

One problem of the presently available methods for producing biofuel is that the yield of biofuel obtained from the method is not high enough to keep a low price of the biofuel in order to make it competitive to conventionally used mineral oils.

Hence, it has been of interest to combine the production of biofuel with the production of alternative valuable by-products. One such product may be protein, which traditionally is isolated from the distillate after e.g. ethanol has been removed from the suspension, by distillation. The problem with this method is that the protein will denature during the high temperature treatment of the distillation process and the only applicability of the protein produced is as an animal supplement.

To overcome this problem, proteins were suggested separated from the suspension before distillation to obtain the ethanol. However, protein products obtained by this method showed to have a very high content of impurities because of unspecific methods used making them unsuitable for human consumption. Use of conventional chromatography, packed bed adsorption techniques, was suggested in order to provide more pure protein products, however, this showed to be undesirable because the production costs became much too high and the production time was also increased to an undesirable extent.

Hence, an improved method for producing biofuel and protein which has a high degree of productivity per unit cost, which is fast, which is reproducible, which requires a minimum of handling steps, which is specific in order to limit the extent of impurities in the protein product and which preferably be compatible with automated and semi-automated systems for optimising performances of the isolation of biofuel and the purification of protein product would be advantageous.

SUMMARY OF THE INVENTION

Thus, it is an object of the present invention to provide a method and a system that solves the above mentioned problems of the prior art with the production of biofuel and protein products.

Therefore, one aspect of the invention relates to a method for providing an isolated biofuel and a purified protein product from a raw material suitable for the production of the biofuel or a derivative of said raw material. The method comprises the steps of:
  (i) subjecting the raw material or a derivative of said raw material to at least one first treatment liberating the biofuel from the raw material or the derivative of said raw material,
  (ii) isolating the biofuel liberated in step (i) obtaining the isolated biofuel,
  (iii) subjecting the raw material or a derivative of said raw material to at least one second treatment providing a material suspension, and
  (iv) subjecting the material suspension from step (iii) to an expanded bed adsorption process obtaining the purified protein product.

Another aspect of the present invention relates to a method for providing an isolated biofuel and a purified protein product from a raw material suitable for the production of the biofuel or a derivative of said raw material. The method comprises the steps of:
  (i) subjecting the raw material or a derivative of said raw material to at least one first treatment liberating the biofuel from the raw material or the derivative of said raw material,
  (ii) isolating the biofuel liberated in step (i) obtaining the isolated biofuel,
  (iii) subjecting the raw material or a derivative of said raw material to at least one second treatment providing a material suspension,
  (iv) subjecting the material suspension from step (iii) to an adsorption process obtaining the purified protein product, and
wherein the yield of protein obtained is an equivalent of at least 10 gram of 100% pure protein product per kg biofuel on a dry matter basis.

Yet another aspect of the present invention is to provide a system for the combined production of an isolated biofuel and a purified protein product from a raw material suitable for the production of the biofuel or a derivative of said raw material. The system comprises:
  (a) a first means for subjecting the raw material or the derivative of said raw material to at least one first treatment for liberating the biofuel from the raw material or the derivative of said raw material, (b) a second means for isolating the liberated biofuel from the raw material or the derivative of said raw material, (c) a third means for subjecting the raw material or the derivative of said raw material to at least one second treatment providing a material suspension, and (d) an expanded bed adsorption column for providing the purified protein product.

The present invention will now be described in more detail in the following.

DETAILED DESCRIPTION OF THE INVENTION

The production of biofuels to replace combustible oil and natural gas is very interesting because it is an efficient way to provide a high energy yield from the efficient production of liquid and gas biofuels based on cheap organic matter (usually cellulose, agricultural and sewage waste). Furthermore, biofuels are considered to be very environmental-friendly as the carbon in biofuels may have been extracted from atmospheric carbon dioxide by growing plants. Therefore, burning these plants does not result in a net increase of carbon dioxide in the Earth's atmosphere. As a result, biofuels may be seen by many as a way to reduce the amount of carbon dioxide released into the atmosphere by using them to replace non-renewable sources of energy.

Thus, in an embodiment of the present invention relates to a method for providing an isolated biofuel and a purified protein product from a raw material suitable for the production of the biofuel or a derivative of said raw material. The method comprises the steps of:

(i) subjecting the raw material or a derivative of said raw material to at least one first treatment liberating the biofuel from the raw material or the derivative of said raw material, (ii) isolating the biofuel liberated in step (i) obtaining the isolated biofuel, (iii) subjecting the raw material or a derivative of said raw material to at least one second treatment providing a material suspension, (iv) subjecting the material suspension from step (iii) to an adsorption process obtaining the purified protein product, and wherein the yield of protein obtained is an equivalent of at least 10 gram of 100% pure protein product per kg biofuel on a dry matter basis.

In the present context the term "an equivalent of at least 10 gram of 100% pure protein product" relates to the amount of protein present in the product wherein the amount of non-protein material has been taken out from the calculation of the protein content. This is also indicated by the statement "of 100% pure protein product" which also demonstrates that it is only the protein product composition which is relevant and not non-protein material.

Non-protein material relates to material not comprising of large organic compounds made of amino acids arranged in a linear chain and joined together between the carboxyl atom of one amino acid and the amine nitrogen of another by a peptide bond. Non-protein material may be, but it not limited to fat, sugar, DNA, lipids etc.

In a preferred embodiment or the present invention the yield of protein obtained may be an equivalent of at least 10 gram of 100% pure protein product per kg biofuel on a dry matter basis, such as at least 20 gram of 100% pure protein product per kg biofuel on a dry matter basis, e.g. at least 30 gram of 100% pure protein product per kg biofuel on a dry matter basis, such as at least 40 gram of 100% pure protein product per kg biofuel on a dry matter basis, e.g. at least 50 gram of 100% pure protein product per kg biofuel on a dry matter basis, such as at least 75 gram of 100% pure protein product per kg biofuel on a dry matter basis, e.g. at least 100 gram of 100% pure protein product per kg biofuel on a dry matter basis, such as at least 150 gram of 100% pure protein product per kg biofuel on a dry matter basis, e.g. at least 200 gram of 100% pure protein product per kg biofuel on a dry matter basis.

The method of the present invention may be a continuous method of providing a biofuel and a protein product. In the present invention the term "continuous method" relates to a method which does not involve any spaces or holes in the method or causes any unnecessary delays between each of the operations. Furthermore, the term "continuous method" may also mean that the method may run or function without the need for human physical labour In a further preferred embodiment the present invention relates to a method for providing an isolated biofuel and a purified protein product from a raw material suitable for the production of the biofuel or a derivative of said raw material. The method comprises the steps of:

(i) subjecting the raw material or a derivative of said raw material to at least one first treatment liberating the biofuel from the raw material or the derivative of said raw material, (ii) isolating the biofuel liberated in step (i) obtaining the isolated biofuel, (iii) subjecting the raw material or a derivative of said raw material to a second treatment providing a material suspension, and (iv) subjecting the material suspension from step (iii) to an expanded bed adsorption process obtaining the purified protein product.

In an embodiment of the present invention steps (i) and (ii) are performed before steps (iii) and (iv) are performed.

In another embodiment of the present invention steps (iii) and (iv) are performed before steps (i) and (ii) are performed.

The Raw Material

The method according to the present invention may be targeted for industrial or large-scale fractionation of raw materials for the production of biofuel and protein products.

In an embodiment of the present invention the raw material or the derivative of said raw material is a biofuel comprising raw material or a biofuel comprising derivative of said raw material.

In yet an embodiment of the present invention the raw material suitable for the production of a biofuel or the derivative of said raw material is selected from the group consisting of a plant material, a derivative of a plant material, an animal material or a derivative of an animal material.

Preferably, the plant material or derivative of the plant material is selected from the group consisting of vegetable derived materials, vegetable derived extracts, fruit derived materials, fruit derived extracts, seeds, carbohydrate containing materials, starch containing materials, cellulose containing materials corn, grass, alfalfa, grain, cereal, soybeans, flaxseed, rapeseed, sugar cane, palm material, straw, timber, manure, rice, husks, sewage, peanut, potatoes, biodegradable waste and food leftovers.

Preferably the animal material is selected from fish, fish derived materials, milk, milk derived materials.

In the present context of the present invention the term "derivative of said raw material" relates to any raw material or fraction of raw material obtained from the raw material. The derivative of said raw material may be obtained after subjecting the raw material to any kind of treatment, in particular, but not limited to, extraction, grinding, milling, hacking, squeezing, slicing, abrading, pressing, crushing, chipping, solubilisation suspending, separation or any combination hereof.

The First Treatment

In the context of the present invention the term "first treatment" relates to the treatment of the raw material or the derivative of said raw material which lead to the liberation of the biofuel from the raw material or the derivative of said raw material. Subsequently any liberated biofuel may be isolated from the raw material.

In the present context the terms "liberated biofuel" or "liberating the biofuel" are used interchangeably and relate the biofuel obtained from the raw material after subjecting the raw material to any kind of process causing the formation, excretion, extraction of the biofuel from the raw material.

Generally, many different method exists for liberating the biofuel from the raw material and the first treatment of the raw material may be selected from the group of the following non limiting list of methods consisting of extraction, grinding, milling, hacking, squeezing, slicing, abrading, pressing, crushing, chipping or any combination hereof, preferably the combination of grinding, milling, hacking, slicing, abrading, crushing or chipping followed by extraction, squeezing or pressing.

In a preferred embodiment of the present invention the biofuel may be liberated from the raw material by one or more of the methods selected from the group consisting of pressing, extraction, fermentation or any combination hereof.

In an embodiment of the present invention the biofuel may be obtained directly from the raw material or the derivative of said raw material by pressing the raw material or the derivative of said raw material and/or by subjecting the raw material or the derivative of said raw material to an extraction and/or by subjecting the raw material or the derivative of said raw material to a fermentation process.

Pressing

Biofuels naturally occurring in the raw material or the derivative of said raw material may be obtained by subjecting the raw material or the derivative of said raw material to pressing. In this method the biofuel may be found in the liquid phase obtained. Subsequently the remaining solid phase may be subjected to extraction and/or fermentation to obtain further biofuel form the raw material or the derivative of said raw material.

In an embodiment of the present invention biofuel may be obtained from the raw material or the derivative of said raw material, such as oil seeds, by subjecting the oil seeds to a mechanical treatment, such as pressing with or without the use of organic solvent (e.g. hexane). The biofuel may be extracted mechanically with an oil press or an expeller. Presses range from small, hand-driven models that an individual can build to power-driven commercial presses. Expellers have a rotating screw inside a horizontal cylinder that is capped at one end. The screw forces the seeds or nuts through the cylinder, gradually increasing the pressure. The biofuel escapes from the cylinder through small holes or slots, and the press cake emerges from the end of the cylinder, once the cap is removed. Both the pressure and temperature can be adjusted for different kinds of feedstock. Preparation of the raw material may include removing husks or seed coats from the seeds and separating the seeds from the chaff.

Extraction

Biofuels naturally occurring in the raw material or the derivative of said raw material may be obtained by subjecting the raw material or the derivative of said raw material to an extraction process. Such extraction method may preferably be an aqueous extraction method where the biofuel will form it own liquid phase as it in the most cases will not be mixable with water. Alternatively, the extraction method may be performed using organic solvents. Subsequently the remaining solid phase, from the extraction method, may be subjected to pressing and/or fermentation to obtain further biofuel from the raw material or the derivative of said raw material.

When the biofuel is being liberated from the raw material or the derivative of said raw material, such as the oil seed, by an aqueous extraction method the mechanical pressing step and the possible use of organic solvents (such as hexane) may be avoided. The aqueous extraction procedure may involve the use of enzymes in order to increase the biofuel extraction yield and/or the protein product extraction yield. The biofuel may be separated from the aqueous extract by e.g. floatation, decantation or centrifugation. In the case of aqueous extraction of the biofuel the protein and the biofuel may be extracted from the solids at the same time or sequentially. The oil may be separated from the aqueous extract before or after the protein has been adsorbed and purified from the extract Fermentation Biofuels may be produced, released or synthetically produced by subjecting the raw material or the derivative of said raw material to a fermentation process providing a fermented material comprising the biofuel.

In an embodiment of the present invention the fermentation process is selected from the group consisting of an alcohol fermentation (such as methanol fermentation, ethanol fermentation, propanol fermentation or butanol fermentation), methan fermentation and hydrogen fermentation.

In order to conduct the fermentation process according to the present invention the fermentation may be performed by one or more microorganisms selected from the group consisting of a yeast, a bacteria and an algae.

Preferably, the one or more microorganisms may be a methane producing bacteria. The methane producing bacteria may be selected from the group consisting of species of *Methanobacterium, Methanobrevibacter, Methanothermus, Methanococcus, Methanomicrobium, Methanogenium, Methanospirillum, Methanoplanus, Methanosphaera, Methanosarcina, Methanolobus, Methanoculleus, Methanothrix, Methanosaeta, Methanopyrus* and *Methanocorpusculum*.

Furthermore, the one or more microorganism may be selected from the group consisting of *Saccharomyces cerevisiae, Pichia* spp., *Thermoanaerobacter* spp and *Zymomonas* spp.

The fermentation process according to the present invention provides a fermentation broth comprising a biofuel and the fermentation broth may comprise at least 2% (w/w) biofuel, such as at least 4% (w/w) biofuel, e.g. at least 6% (w/w) biofuel, such as at least 8% (w/w) biofuel, e.g. at least 10% (w/w) biofuel.

The biofuel obtained according to the present invention, preferably by pressing, extraction, fermentation or any combination hereof may be separated from the fermented material by an isolation process.

In an embodiment of the present invention the isolation process may be selected from the group consisting of evaporation, extraction, distillation, centrifugation, decanting and any combination hereof.

A carbohydrate containing raw material optionally subjected to different pre-treatments may be subjected to fermentation using e.g. a yeast strain producing ethanol. Following fermentation the ethanol may be isolated from the fermentation broth by e.g. evaporation/distillation.

The protein produced during the fermentation may be isolated at several different stages of the process:

(i) If the raw material comprises protein it may be purified by an adsorption process at a suitable point prior to the initiation of the fermentation process.

(ii) Alternatively, the protein may be purified from the fermentation broth after fermentation, and before or after, the separation of the biofuel. After fermentation the fermentation broth will comprise proteins and peptides originating from the raw material and proteins originating from the yeast that has been growing in the fermentation medium. Optionally, the yeast cells may be disintegrated in order to release more proteins to the fermentation broth to be purified. The cells may be disintegrated by mechanical or chemical means including high pressure homogenization, bead mill mechanical disruption, sonication and autolysis (enzymes and/or organic solvents may be involved in this step).

(iii) Proteins may alternatively be purified from yeast cells that have first been isolated from the bulk of the fermentation broth. The yeast cells may subsequently be disintegrated to release the protein efficiently as described above The Second Treatment In the context of the present invention the term "second treatment" relates to the treatment of the raw material or the derivative of said raw material which lead to the provision of a suspension can be applied to an adsorption process, preferably to an expanded bed adsorption process, which may be used to purify the protein product.

Various methods exists suitable for the second treating of the raw material or the derivative of said raw material to obtain it as a suspension. Preferably, the second treatment is selected from the group consisting of extraction, solubilisation, grinding, milling, hacking, squeezing, slicing, abrading, pressing, crushing, chipping, suspending and separation or any combination hereof.

Preferably, the raw material or the derivative of said raw material may be suspended in an aqueous solution providing an aqueous material suspension.

Preferably, the first treatment and/or the second treatment may provide a solid and at least one liquid phase.

In an embodiment of the present invention the biofuel and/or the protein product may isolated/purified from the solid phase or a derivative of the solid phase.

In another embodiment of the present invention the biofuel and/or the protein product may be isolated/purified from the liquid phase or a derivative of the liquid phase.

In an embodiment of the present invention a solid phase obtained from the isolation of the liberated biofuel in step (ii) is suspended in an aqueous phase before being subjected to the second treatment and/or before being subjected to an adsorption process, preferably an expanded bed adsorption process, obtaining the purified protein product.

In a further embodiment of the present invention the second treatment may involve extraction of the protein product from the solid remaining after biofuel separation. The solid may be disintegrated by any mechanical means and added water or an aqueous buffer in order to solublise the proteins from the solid. Extraction may be performed at varying temperature, pH and salt concentrations and for varying length of time in order to provide the highest yield of soluble protein. Enzymes may also be added in order to increase the protein extraction yield.

Protein products obtained from the adsorption process (eluted from the adsorbent) may be subjected to an optional ultrafiltration step in order to concentrate the proteins. Preferably, the permeate from the ultrafiltration step may be returned back into the processing of further solids in order to minimize water consumption.

The Adsorption Process

In a preferred embodiment of the present invention the protein product may be purified by an adsorption process. As it is of interest to provide a method for purifying a protein product which is fast, specific in order to limit the extent of impurities in the protein product it is preferred that the adsorption process may be an expanded bed adsorption process or fluidised bed adsorption process, batch adsorption, suspended bed adsorption and membrane based adsorption. Most preferably, the adsorption process may be an expanded bed adsorption.

Among the various industrial chromatographic separation techniques developed in recent years, Expanded Bed Adsorption (EBA) has been successfully introduced to the certain fields of biotechnology industry. EBA is a type of fluidised bed adsorption wherein the level of back-mixing is kept at a minimum. Compared with other chromatographic separation technologies, EBA offer a significant advantage because it can be used directly with non-clarified feed.

During EBA, the adsorbent bed is allowed to expand inside the chromatographic column when a flow of liquid is applied. Expansion of the bed is often effected in a column having provided at each of its ends a net structure covering the cross-sectional area of the column, or some other perforated devices, which will not generate turbulence in the flow. See, for instance, WO-A-9218237 (Amersham Pharmacia Biotech AB, Sweden). The same effect has also been observed in a system utilising a stirred inlet flow WO-A-9200799, (Up-Front Chromatography A/S). In addition, other distributors are likely to be feasible.

In the expanded bed state, the distances between the adsorbent particles result in a free passage of particulate impurities in the feed stream. By contrast, traditional packed beds work as depth filters that can clog, resulting in increased back-pressure unless the feed is thoroughly clarified. Since no significant pressure builds up in an EBA column, it is possible to apply EBA without the limitations in size and flow rate normally associated with packed-bed columns.

Thus, in a preferred embodiment of the present invention the adsorption process does not involve a packed bed.

An EBA process may be characterised by very limited back-mixing of the liquid inside the column as opposed to the well know turbulent fluidised beds. Back-mixing in a bed is often measured as axial dispersion ("vessel dispersion number"), see Levenspiel, "Chemical Reaction Engineering" 2nd Edition, John Wiley & Sons (1972).

Before subjecting the material suspension to the adsorption process the method may further comprises a step of pH adjustment before subjecting the material suspension to the expanded bed adsorption process obtaining a purified protein product.

The purification may be performed efficiently by applying the material suspension to the adsorbent column at a linear flow rates of at least 3 cm/min, such as at least 5 cm/min, e.g. at least 8 cm/min, such as at least 10 cm/min e.g. 20 cm/min. Typically the flow rate is selected in the range of 5-50 cm/min, such as in the range of 5-15 cm/min, e.g. in the range of 10-30 cm/min, such as in the range of 25-50 cm/min.

When the material suspension is added to the adsorbent column the ratio between the adsorbent particle present in the column and the material suspension may be optimized in order to retain a high capacity of the adsorbent column and to obtain a high purity of the protein product to be purified. In a preferred embodiment of the present invention the adsorbent present in the column relative to the protein-containing mixture to be loaded on to the column are provided at a ratio of at least 1:1000, such as at least 1:800, e.g. at least 1:600, such as at least 1:400, e.g. at least 1:300, such as at least 1:200, e.g. at least 1:100, such as at least 1:50, e.g. at least 1:30, such as at least 1:15, e.g. 1:10, such as 1:5 measured on a volume/volume basis.

In order to obtain the purified protein product the elution may be performed by any method conventionally described and known in the prior art.

In an alternative and very suitable embodiment of the present invention, the elution of the adsorbed protein product may be performed with a solution, typically selected from the group consisting of dilute base, dilute acid, and water. In the embodiment wherein the eluting or washing step is performed with such a solution, the solution is dilute so as to minimise the amount of salt and other unwanted substances present in the eluted product.

Preferably, the dilute acid or base used for elution of the biomolecular substance has a salt concentration of less than 50 mM, preferably less than 30 mM, even more preferable less than 20 mM. The determination of the salt concentration is performed directly on the eluate fraction containing the protein or proteins to be isolated without additional dilution of the eluate fraction. Common, low cost and non-toxic acids and bases are applicable. Specifically preferred are the bases sodium hydroxide (NaOH), potassium hydroxide (KOH), calcium hydroxide (Ca(OH)$_2$), ammonium hydroxide (NH$_4$OH).

In an embodiment of the present invention elution may be performed using an eluent comprising less than 5% (v/v) of organic solvents, such as less than 3% (v/v) of organic solvent, e.g. less than 1% (v/v) organic solvent, such as 0% (v/v) of organic solvent.

The Adsorbent

The adsorption process according to the present invention involves an adsorbent.

In the present context the term "adsorbent" relates to the entire bed present in an adsorbent column and the term "adsorbent particle" are used interchangeably with the term "particle" and relates to the individual single particles which makes up the adsorbent.

The flow rate, the size of the particles and the density of the particles may all have influence on the expansion of the fluid bed and it is important to control the degree of expansion in such a way to keep the particles inside the column. The degree of expansion may be determined as H/H0, where H0 is the height of the bed in packed bed mode and H is the height of the bed in expanded mode. In a preferred embodiment of the present invention the degree of expansion H/H0 is in the range of 1.0-20, such as 1.0-10, e.g. 1.0-6, such as 1.2-5, e.g. 1.5-4 such as 4-6, such as 3-5, e.g. 3-4 such as 4-6. In an other preferred embodiment of the present invention the degree of expansion H/H0 is at least 1.0, such as at least 1.5, e.g. at least 2, such as at least 2.5, e.g. at least 3, such as at least 3.5, e.g. at least 4, such as at least 4.5, e.g. at least 5, such as at least 5.5, e.g. at least 6, such as at least 10, e.g. at least 20.

The density of the adsorbent particle may be at least 1.3 g/mL, more preferably at least 1.5 g/mL, still more preferably at least 1.8 g/mL, even more preferably at least 2.0 g/mL, more preferably at least 2.3 g/mL, even more preferably at least 2.5 g/mL, most preferably at least 2.8 g/mL in order to enable a high productivity of the process.

In a preferred embodiment of the present invention the adsorbent particle has a mean particle size of at most 150 µm, particularly at most 120 µm, more particularly at most 100 µm, even more particularly at most 90 µm, even more particularly at most 80 µm, even more particularly at most 70 µm. Typically the adsorbent particle has a mean particle size in the range of 40-150 µm, such as 40-120 µm, e.g. 40-100, such as 40-75, e.g. 40-50 µm.

In a combination of preferred embodiments, where the average particle diameter is 150 µm or less the particle density is at least 1.5 g/ml, such as at least 1.8 g/ml. When the average particle size is 120 µm or less, the particle density is at least 1.6 g/mL, more preferably at least 1.9 g/mL. When the average particle diameter is less than 90 µm the density must be at least 1.8 g/mL or more preferable at least 2.0 g/mL. When the average particle diameter is less than 75 µm the density must be at least 2.0 g/mL, more preferable at least 2.3 g/mL, more preferable at least 2.5 g/mL and most preferable at least 2.8 g/mL.

The high density of the adsorbent particle is, to a great extent, achieved by inclusion of a certain proportion of a dense non-porous core materials, preferably having a density of at least 4.0 g/mL, such as at least 5.0. Typically, the non-porous core material has a density in the range of about 4.0-25 g/ml, such as about 4.0-20 g/ml, e.g. about 4.0-15 g/mL, such as 12-19 g/ml, e.g. 14-18 g/ml, such as about 6.0-15.0 g/mL, e.g. about 6.0-10 g/ml.

In an embodiment of the present invention the adsorbent comprising a particle having a functionalized matrix polymer carrying a plurality of covalently attached functional groups comprising an aromatic or heteroaromatic ring-system and/or one or more acidic groups.

Preferably the functional groups comprising an aromatic or heteroaromatic ring-system and/or one or more acid groups have a molecular weight of at the most 500 Dalton.

In an embodiment of the present invention the functional groups comprising an aromatic or heteroaromatic ring-system and/or one or more acid groups forms a ligand or part of a ligand with affinity to proteins.

In an embodiment of the present invention the heteroaromatic moiety may be selected from monocyclic heteroaromatic radicals selected from thiophene, furan, pyran, pyrrole, imidazole, pyrazole, isothiazole, isoxazole, pyridine, pyrazine, pyrimidine, and pyridazine radicals; and bicyclic heteroaromatic radicals selected from indole, purine, quinoline, benzofuran, benzimidazole, benzothiazole, and benzoxazole radicals.

In a further embodiment of the present invention the acidic group is selected from a carboxylic acid group (—COOH), a sulfonic acid group (—S$_2$OH), sulfinic acid group (—S(O)OH), phosphinic acid group (—PH(O)(OH)), phosphonic acid monoester groups (—P(O)(OH)(OR)), and phosphonic acid group (—P(O)(OH)$_2$).

Preferably, the functional groups comprising an aromatic or heteroaromatic ring-system and/or one or more acid groups may be derived from compounds selected from dihydroxy-benzoic acids, amino-benzoic acids, diamino-benzoic acids, mercapto-benzoic acids, mercapto-nicotinic acids, mercapto-tetrazole acetic acids, benzimidazoles, benzothiazoles, benzoxazoles, diacids, 2,5-dihydroxy-benzoic acid, 2-amino-benzoic acid, 3-amino-benzoic acid, 4-amino-benzoic acid, 2-mercapto-benzoic acid, 2-mercapto-nicotinic acid, 5-mercapto-1-tetrazole acetic acid, 2-mercapto-benzimidazole, 4-aminophthalic acid, and 5-aminoisophthalic acid.

In an embodiment of the present invention the concentration of the functional groups comprising an aromatic or heteroaromatic ring-system and/or one or more acid groups is in the range of 10-990 µmol/g dry matter of solid phase matrix.

In yet an embodiment of the present invention the concentration of the functional groups comprising an aromatic or heteroaromatic ring-system and/or one or more acid groups is in the range of 1-145 µmol/ml of hydrated, sedimented solid phase matrix.

In a further embodiment of the present invention the concentration of the functional groups comprising an aromatic or heteroaromatic ring-system and/or one or more acid groups is in the range of 1-130 µmol/g wet, but suction drained solid phase matrix.

The non-porous core constitutes typically of at most 50% of the total volume of the adsorbent particle, such as at most 40%, preferably at most 30%.

The adsorbent particle used according to the invention may be at least partly permeable to the biomolecular substance to be isolated in order to ensure a significant binding capacity in contrast to impermeable particles that can only bind the target molecule on its surface resulting in relatively low binding capacity. The adsorbent particle may be of an array of different structures, compositions and shapes.

Thus, the adsorbent particles may be constituted by a number of chemically derivatised porous materials having the necessary density and binding capacity to operate at the given flow rates per se. The particles are either of the conglomerate type, as described in WO 92/00799, having at least two non-porous cores surrounded by a porous material, or of the pellicular type having a single non-porous core surrounded by a porous material.

In the present context the term "conglomerate type" relates to a particle of a particulate material, which comprises beads of core material of different types and sizes, held together by the polymeric base matrix, e.g. an core particle consisting of two or more high density particles held together by surrounding agarose (polymeric base matrix).

In the present context the term "pellicular type" relates to a composite of particles, wherein each particle consists of only one high density core material coated with a layer of the porous polymeric base matrix, e.g. a high density stainless steel bead coated with agarose.

Accordingly the term "at least one high density non-porous core" relates to either a pellicular core, comprising a single high density non-porous particle or it relates to a conglomerate core comprising more that one high density non-porous particle.

The adsorbent particle, as stated, comprises a high density non-porous core with a porous material surrounding the core, and said porous material optionally comprising a ligand at its outer surface.

In the present context the term "core" relates to the non-porous core particle or core particles present inside the adsorbent particle. The core particle or core particles may be incidental distributed within the porous material and is not limited to be located in the centre of the adsorbent particle.

Examples of suitable non-porous core materials are inorganic compounds, metals, heavy metals, elementary non-metals, metal oxides, non metal oxides, metal salts and metal alloys, etc. as long as the density criteria above are fulfilled. Examples of such core materials are metal silicates metal borosilicates; ceramics including titanium diboride, titanium carbide, zirconium diboride, zirconium carbide, tungsten carbide, silicon carbide, aluminum nitride, silicon nitride, titanium nitride, yttrium oxide, silicon metal powder, and molybdenum disilide; metal oxides and sulfides, including magnesium, aluminum, titanium, vanadium, chromium, zirconium, hafnium, manganese, iron, cobalt, nickel, copper and silver oxide; non-metal oxides; metal salts, including barium sulfate; metallic elements, including tungsten, zirconium, titanium, hafnium, vanadium, chromium, manganese, iron, cobalt, nickel, indium, copper, silver, gold, palladium, platinum, ruthenium, osmium, rhodium and iridium, and alloys of metallic elements, such as alloys formed between said metallic elements, e.g. stainless steel; crystalline and amorphous forms of carbon, including graphite, carbon black and charcoal. Preferred non-porous core materials are tungsten carbamide, tungsten, steel and titanium beads such as stainless steel beads.

The porous material is a polymeric base matrix used as a means for covering and keeping multiple (or a single) core materials together and as a means for binding the adsorbing ligand.

The polymeric base matrix may be sought among certain types of natural or synthetic organic polymers, typically selected from i) natural and synthetic polysaccharides and other carbohydrate based polymers, including agar, alginate, carrageenan, guar gum, gum arabic, gum ghatti, gum tragacanth, karaya gum, locust bean gum, xanthan gum, agaroses, celluloses, pectins, mucins, dextrans, starches, heparins, chitosans, hydroxy starches, hydroxypropyl starches, carboxymethyl starches, hydroxyethyl celluloses, hydroxypropyl celluloses, and carboxymethyl celluloses; ii) synthetic organic polymers and monomers resulting in polymers, including acrylic polymers, polyamides, polyimides, polyesters, polyethers, polymeric vinyl compounds, polyalkenes, and substituted derivatives thereof, as well as copolymers comprising more than one such polymer functionally, and substituted derivatives thereof; and iii) mixture thereof.

A preferred group of polymeric base matrices are polysaccharides such as agarose.

The ligand of attached to the adsorbents typically provides a dynamic binding capacity of at least 10 g of biomolecular substance per liter, more preferably at least 20 g per liter, still more preferable at least 30 g per liter when tested according to the process conditions used in the relevant application. The binding capacity of the adsorbent may be determined in terms of its binding capacity to bovine serum albumin (BSA). The binding capacity of the adsorbent is typically such that at least 10 g/L of BSA binds according to test Method A.

Method A is a method used for determination of the bovine albumin binding capacity of selected adsorbents consisting of the following process:

Bovine serum albumin solution pH 4.0 (BSA pH 4.0): Purified bovine serum albumin (A 7906, Sigma, USA) is dissolved to a final concentration of 2 mg/ml in 20 mM sodium citrate pH 4.0. Adsorbents are washed with 50 volumes of 20 mM sodium citrate pH 4.0 and drained on a suction filter.

A sample of 1.0 ml suction drained adsorbent is placed in a 50 ml test tube followed by the addition of 30 ml of BSA, pH 4.0.

The test tube is then closed with a stopper and the suspension incubated on a roller mixer for 2 hours at room temperature (20-25° C.). The test tube is then centrifuged for 5 min. at 2000 RPM in order to sediment the adsorbent completely. The supernatant is then isolated from the adsorbent by pipetting into a separate test tube, avoiding the carry-over of any adsorbent particles and filtered through a small non-adsorbing 0.2 µm filter (Millipore, USA). Following this a determination of the concentration of non-bound BSA in the supernatant is performed by measuring the optical density (OD) at 280 nm on a spectrophotometer.

The amount of BSA bound to the adsorbent is then calculated according to the following formula:

mg BSA bound per ml suction drained adsorbent=(1−(OD of test supernatant/OD of BSA starting solution))×60 mg BSA/ml adsorbent.

The Further Treatment

The raw material or a derivative of said raw material may be subjected to a further treatment resulting in a partially hydrolysed raw material.

Such further treatment involves a wet oxidation, a steam explosion or enzyme treatment.

Preferably, the raw material and/or the partial hydrolysed raw material is subjected to a hydrolysis selected from the group consisting of an enzyme hydrolysis, an acid hydrolysis or an alkaline hydrolysis resulting in an increased liberation of biofuel and/or a material suspension comprising increased amount of fermentable sugars and/or increased amount of soluble proteins.

The wet oxidation process takes traditionally place in an aqueous medium in the presence of an oxidising agent which reacts oxidatively with the components present in the solid phase. Steam explosion is a thermal-mechanical-chemical process that combines the presence of heat (as steam), mechanical forces (shearing effect) and chemical action (hydrolysis). The result of the two pre-treatments is the alteration of the microfibrillar packing inside the cell wall and the rupture of the fibre, which causes an increase in the accessibility of the cellulose to hydrolytic enzymes. The optimum temperature and reaction time conditions in the processes vary depending on the kind of material.

After the further treatment, the partial separated material may be treated with enzymes to release sugars that can be fermented to ethanol as well as biofuel and/or protein products.

Both the new solid phase and the new liquid phase obtained from this further treatment may be used for the production of biofuel and/or protein products as a derivative of the raw material.

The Biofuel

In a preferred embodiment of the present invention biofuel may be selected from the group consisting of oil, methanol, methane, ethanol, propanol, butanol, hydrogen and biodiesel, however, the biofuel is not limited to the listed biofuels other obvious biofuels that can be produced by the present process are also included.

The Protein Product

In the present context the term "protein product" relates to a single protein or a mixture of one or more proteins comprising of amino acids arranged in a linear chain and joined together between the carboxyl atom of one amino acid and the amine nitrogen of another by peptide bonds.

In an embodiment of the present invention, the protein product comprises a limited amount of non-protein material, such as fat, sugar, DNA, lipids etc. Preferably, the protein product comprises at the most 20% (w/w) non-protein material, such as at most 15% (w/w) non-protein material, e.g. at most 10% non-protein material, such as at most 5% (w/w) non-protein material, e.g. at most 2% non-protein material, such as at most 1% (w/w) non-protein material, e.g. at most 0.5% non-protein material.

In a further embodiment of the present invention at least 50% of the protein product may be composed of a single protein, such as at least 60% of the protein product may be composed of a single protein, e.g. at least 70% of the protein product may be composed of a single protein, such as at least 80% of the protein product may be composed of a single protein, e.g. at least 90% of the protein product may be composed of a single protein such as at least 95% of the protein product may be composed of a single protein, e.g. at least 98% of the protein product may be composed of a single protein such as at least 99% of the protein product may be composed of a single protein.

The System

The present invention is further directed to a system for the combined production of an isolated biofuel and a purified protein product from a raw material suitable for the production of the biofuel or a derivative of said raw material, said system comprises:

(a) a first means for subjecting the raw material or the derivative of said raw material to a first treatment for liberating the biofuel from the raw material or the derivative of said raw material, (b) a second means for isolating the liberated biofuel from the raw material or the derivative of said raw material, (c) a third means for subjecting the raw material or the derivative of said raw material to a second treatment providing a material suspension, and (d) an adsorption column for providing the purified protein product.

In an embodiment of the present invention the first container and the second container are the same.

In yet an embodiment of the present invention the first container, the second container, the means for isolating the liberated biofuel and the adsorption column may be interconnected.

The first container, the second container, the means for isolating the liberated biofuel and the adsorption column may form a closed system for producing biofuel and a protein product. In the present context the term "closed system" relates to a system where the first container, the second container, the means for isolating the liberated biofuel and the adsorption column are all connected to each other. This means that there are no spaces or holes between the first container, the second container, the means for isolating the liberated biofuel and the expanded bed adsorption column.

Preferably, the adsorbent column may be selected from the group consisting of expanded bed adsorption column or fluidised bed adsorption column, batch adsorption column, suspended bed adsorption column and membrane based adsorption column. Most preferably, the adsorption column may be an expanded bed column.

In an embodiment of the present invention the first container is connected to the means for isolating the liberated biofuel which is connected to the second container and then connected to the adsorption column.

In yet an embodiment of the present invention the first container is connected to the means for isolating the liberated biofuel which is connected to the adsorption column.

In a further embodiment of the present invention the first container is connected to the adsorption column which is connected to the means for isolating the liberated biofuel.

In still an embodiment of the present invention the first container is connected to the means for isolating the liberated biofuel and to the second container and the second container is connected to the adsorption column.

In still another embodiment of the present invention the first container is connected to the means for isolating the liberated biofuel and to the adsorption column.

In still a further embodiment of the present invention the first means and third means may be selected independent from each other from the group consisting of a container, pressing device, an extraction device, a filtration device, evaporation device, a fermenting device and distillation device.

In yet an embodiment of the present invention the second means may be selected independent from each other from the group consisting of a container, pressing device, an extraction device, a filtration device, evaporation device, a and distillation device.

Further Embodiments

The protein product according to the present invention may be purified at many different stages of the method. These different stages include, but are not limited to:
- the protein product may be purified before the biofuel may be isolated,
- the raw material or a derivative of said raw material may be subjected to pressing and optionally extraction followed by purification of the protein product before isolation of the biofuel,
- the biofuel may be isolated before the protein product may be purified,
- the raw material or a derivative of said raw material may be subjected to pressing and optionally extraction followed by isolation of the biofuel before the protein product may be purified,
- the protein product may be purified after the raw material or a derivative of said raw material has been subjected to pressing and optionally extraction and before the fermentation in step (ii) may be performed,
- the raw material or a derivative of said raw material may be subjected to extraction and optionally pressing followed by purification of the protein product before isolation of the biofuel,
- the raw material or a derivative of said raw material may be subjected to extraction and optionally pressing followed by isolation of the biofuel before the protein product may be purified, or
- the protein product may be purified after the raw material or a derivative of said raw material has been subjected to extraction and optionally pressing and before the fermentation in step (ii) may be performed.

It should be noted that embodiments and features described in the context of one of the aspects of the present invention also apply to the other aspects of the invention.

The invention will now be described in further details in the following non-limiting embodiment.

EMBODIMENTS OF THE PRESENT INVENTION

Embodiment 1

Production of protein and a biofuel from oil seeds. The method comprises the following steps:
(i) Subjecting the oil seeds to a mechanical treatment, such as pressing with or without the use of organic solvent (e.g. hexane). biofuel can be extracted mechanically with an oil press or an expeller. Presses range from small, hand-driven models that an individual can build to power-driven commercial presses. Expellers have a rotating screw inside a horizontal cylinder that is capped at one end. The screw forces the seeds or nuts through the cylinder, gradually increasing the pressure. The biofuel escapes from the cylinder through small holes or slots, and the press solid emerges from the end of the cylinder, once the cap is removed. Both the pressure and temperature can be adjusted for different kinds of feedstock. Preparation of the Raw Material or the Derivative of Said Raw Material May Include removing husks or seed coats from the seeds and separating the seeds from the chaff.
(ii) Extracting the protein product from the solid remaining after biofuel separation. The solid may be disintegrated by any mechanical means and added water or an aqueous buffer in order to solubilise proteins from the solid. Extraction may be performed at varying temperature, pH and salt concentrations and for varying length of time in order to provide the highest yield of soluble protein. Enzymes may also be added in order to increase the protein extraction yield.
(iii) The protein extract may be subjected to an adsorption process, involving an adsorbent which is not packed in a column during the adsorption step, but rather suspended in a stirred tank, a fluidised bed or an expanded bed.
(iv) Optionally, the protein product obtained from the adsorption process (eluted from the adsorbent) may be subjected to an ultrafiltration step in order to concentrate the protein product. The permeate from the ultrafiltration step may be returned back into the processing of further seed cake in order to minimize water consumption.
(v) The unbound fraction from step (iii) may be concentrated by different means including evaporation, distillation and membrane filtration and any condensate or permeate water may be returned to the processing/extraction of further seed solid.

The biofuel may also be liberated from the oil seed by an aqueous extraction method thus avoiding the mechanical pressing step and the possible use of organic solvents (such as hexane). The aqueous extraction procedure may involve the use of enzymes in order to increase the biofuel extraction yield and/or the protein extraction yield. The biofuel may be separated from the aqueous extract by e.g. floatation, decantation or centrifugation. In the case of aqueous extraction of the biofuel the protein and the biofuel may be extracted from the solids at the same time or sequentially. The biofuel may be separated from the aqueous extract before or after the protein has been adsorbed and isolated from the extract.

Embodiment 2

Production of protein and a biofuel produced by fermentation of a raw material. The method comprises the following steps:
(i) A carbohydrate containing raw material optionally subjected to different pre-treatments is subjected to fermentation using e.g. a yeast strain producing ethanol. Following fermentation the ethanol may be isolated from the fermentation broth by e.g. evaporation and/or distillation.
(ii) The protein may be isolated at several stages of the process:
  (a) If the raw material comprises protein products it may be purified by an adsorption process at a suitable point prior to the initiation of the fermentation process.
  (b) Alternatively, protein product may be purified from the fermentation broth after fermentation, and before or after, the separation of the biofuel.
  After fermentation the fermentation broth will comprise proteins and peptides originating from the raw material and proteins originating from the yeast that has been growing in the fermentation medium. The yeast cells may be disintegrated by mechanical or chemical means including high pressure homogenization, bead mill mechanical disruption, sonication and autolysis (enzymes and/or organic solvents may be involved in this step).
  (c) The protein product may also be purified from yeast cells that have first been separated from the bulk of the fermentation broth. The yeast cells may be disintegrated to release the protein efficiently as described above and then subjected to an adsorption process.

EXAMPLES

| | Abbreviations |
|---|---|
| DEAE | Diethylaminoethyl |
| MBS | Mercapto benzoic acid |
| NaCi | Sodium citrate |
| NaCl | Sodium chloride |
| SDS-PAGE | Sodium dodecyl sulphate - poly acrylamide gel electrophoresis |
| SP | Sulfo propyl |

Example 1

Isolation of Proteins and Production of Ethanol from Wheat

Isolation of wheat proteins with expanded bed adsorption chromatography at 25° C.:

Extraction

A wheat extract was obtained by mixing 1 kg of finely ground dehulled wheat grains with 10 L 25 mM NaCl in water. The suspension was mechanically stirred at 100 rpm for 1 hour at 25° C. The wheat extract was then centrifuged to obtain a clear liquid phase and a sediment comprising insoluble materials such as gluten and starch. The total volume of collected extract was 9.5 L. The remaining sedimented, wet material is kept for later ethanol production.

Expanded Bed Adsorbent

The adsorbent was based on cross-linked agarose beads with integrated tungsten carbide particles resulting in a high density matrix of approximately 2.8 g/ml. The particle size was in the range of 40-200 μm with a mean volume diameter of 150 micron. Several adsorbents comprising varying ligands that generally bind proteins in the pH range of 4-6 were tested for binding efficiency.

Pre-Treatment of the Wheat Extract

The pH in the extract was adjusted to different values in the range of pH 4-6 with 1 M hydrochloric acid in different experiments.

The experiments were performed in a FastLine® 10 expanded bed column (Ø=2 cm), UpFront Chromatography A/S, Copenhagen, Denmark. The column was packed with H0=50 cm of adsorbent (157 ml) and equilibrated with a solution of 10 mM NaCl having the same pH as the start material, at 25° C.

In different experiments (Experiment A-C) the wheat flour extract at different pH values was loaded onto the column with a linear flow rate of 10 cm/min. For each experiment 3140 ml extract was loaded and following a brief wash of the column with water (approx. 150 ml wash) elution of bound proteins was performed with 50 mM NaOH.

The concentration of protein in the eluates was estimated by Nitrogen-determination (N×6.25). Analysis by SDS-PAGE was also performed (gels from the SDS-PAGE are not shown).

Results

| Experiment | Ligand | pH-value during adsorption | Protein yield in eluate mg protein/ml extract | Protein yield in eluate g protein/kg wheat grain |
|---|---|---|---|---|
| A | SP 4% | 4.0 | 2.3 | 21.4 |
| B | 4-MBS 6% | 4.5 | 2.2 | 20.5 |
| C | DEAE 6% | 6.0 | 1.5 | 14.0 |

The maximal amount of protein eluate was thus 21.4 gram protein/kg dry wheat grain (experiment A).

SDS-PAGE analysis of each experiment was performed and showed that substantially all the proteins present in the starting material (the wheat extract) is bound to the column, since the run-through fraction and washing fraction is practically devoid of protein, while the eluate comprise grossly the same protein composition as the starting material. Similar results were obtained with example B and C with a slightly lower content of the protein bound. Thus, all three adsorbents showed to bind a high extent of the proteins present in the wheat extract, but to a slightly varying degree. The eluted protein compositions obtained from all the experiments A, B and C also showed a content of non-protein material less than 10% on a dry matter basis.

Ethanol Production

The run-through fractions from experiment A-C, which was practically depleted for protein by the adsorption procedure above, was combined and mixed back with the sedimented material obtained by the extraction and sedimentation above, to create a suspension comprising wheat starch. This recombined suspension was then added amyloglucosidase (300 AGU/kg starch) and heated to 55° C. for 8 hours to perform a saccharification of the starch material. Following saccharification the suspension was cooled to 35° C. and added Saccharomyces cerevisiae to perform the fermentation for 56 hours. Following fermentation the ethanol was distilled and collected. The yield of ethanol corresponded to 0.3 L/kg dry wheat grain.

The maximal yield of protein per L ethanol produced thus corresponds to:

21.4 gram protein/0.3=71.3 gram protein/L ethanol produced.

Example 2

Isolation of Proteins and Production of Ethanol from Wheat

Finely ground and dehulled wheat grain was extracted as described in example 1. Prior to centrifugation the extract was separated into (i) a concentrated fraction rich in insoluble starch (underflow) and (ii) another fraction comprising the insoluble gluten and soluble proteins (overflow) by passing the crude extract through a battery of hydrocyclones. The hydrocyclone overflow comprising the bulk of the liquid extract and the soluble proteins were then sedimented and decanted to obtain a sedimented gluten fraction and a clarified extract comprising the soluble proteins. The extract was then adsorbed for proteins as described in example 1b and the protein-depleted run-through fraction was returned and mixed back with the starch fraction from the hydrocyclone underflow. The starch was suspended in the returned protein depleted liquid added amyloglucidase for saccharification and fermented with Saccharomyces cerevisiae as described in example 1.

Results

The protein yield from the adsorption step corresponded to 20.1 gram per kg wheat grain and the ethanol yield corresponded to 0.3 L per kg wheat grain. The yield of protein from the adsorption step corresponded to 67 gram protein per L ethanol produced.

Example 3

Isolation of Soybean Oil and Soluble Proteins

Oil Extraction

Dry soybeans were milled into flour in a coffee mill. Approximately 100 gram of the flour was mixed with 200 ml of isopropanol and stirred for 30 min. The pellet was here after allowed to sediment for 10 min. The supernatant was decanted into a beaker with a large surface area in order to evaporate the isopropanol. The pellet was washed 4 times with 100 ml of isopropanol. The supernatant and washes were all pooled. The pool and the pellet were left in a fume cupboard for the isopropanol to evaporate over night. After evaporation of the isopropanol the yellow oil phase weighed 16.5 gram, corresponding to 0.165 L oil per kg ground soybeans.

Protein Extraction

The dried soybean flour depleted for oil by extraction with isopropanol was mixed with 300 ml water and stirred for 1 hour. The soybean extract was collected by filtration on a 100 μm net. The filter cake was washed with 150 ml of water. The total volume of collected extract was 350 ml.

Expanded Bed Adsorbent

The adsorbent was based on cross-linked agarose beads with integrated tungsten carbide particles resulting in a high density matrix of approximately 2.8 g/ml. The particle size was in the range of 40-200 μm with a mean volume diameter of 150 micron. Several adsorbents comprising varying ligands that generally bind proteins in the pH range of 4-6 were tested for binding efficiency.

Pre-Treatment of the Extract

The pH in the extract was adjusted to different values in the range of 4-6 with 1 M hydrochloric acid in different experiments (experiment A-E).

The experiment was performed in a FastLine® 10 expanded bed column (Ø=1 cm), UpFront Chromatography A/S, Copenhagen, Denmark. The column was packed with H0=50 cm of adsorbent (39.2 ml) and equilibrated with a solution of 10 mM NaCl having a pH equal to the start material, at 25° C.

The soybean extract at different pH values was loaded onto the column with a linear flow rate of 10 cm/min. 60 ml extract was loaded followed by a brief was with water (50 ml). Elution of the bound protein was performed with 50 mM NaOH. The concentration of protein in the eluates was estimated by Nitrogen determination (Kjeldahl, N×6.25). Analysis by SDS-PAGE was also performed.

Results

| Experiment | Ligand | pH-value during adsorption | Protein yield in eluate g protein/ kg soybean |
|---|---|---|---|
| A | SP | 4.0 | 31.3 |
| B | SP | 5.0 | 47.0 |
| C | 4-MBS | 4.5 | 54.8 |
| D | 4-MBS | 5.0 | 76.1 |
| E | DEAE | 6.0 | 44.9 |

SDS-PAGE analysis of samples (filtered on 1 micron filter) for each experiments A-E were performed and showed that practically all the proteins solubilised and present in the extracts were bound to en expanded bed adsorbent (since the run-through fractions and the wash fractions is substantially devoid of protein to different levels. Subsequently the proteins bound are eluted into the eluate. The eluted protein compositions obtained from all the experiments A-E also showed a content of non-protein material less than 10% on a dry matter basis.

All SDS-PAGE analyses were performed non-reduced and stained with coomassie blue.

The highest protein yield of 76.1 g protein/kg soybeans was obtained in experiment D using an adsorbent comprising a 4-mercaptobenzoic acid ligand at pH 5.0.

Thus the highest protein yield per L soybean oil corresponds to:

(76.1 g protein/kg)/(0.165 L oil/kg)=461 g protein/L soybean oil.

REFERENCES

WO-A-9218237, "Process and means for down stream processing," by Carlsson et al., published 29 Oct. 1992.
WO-A-9200799, "Substance carrying conglomerate" by Lihme et al., published 23 Jan. 1992.

The invention claimed is:

1. A method for isolating a biofuel and a purified protein product from a raw material derived from a plant or an animal, wherein said biofuel is an oil, said method comprising the steps of:
   (i) treating the raw material to liberate the oil from the raw material and to provide a protein-containing residue,
   (ii) isolating the oil liberated in step (i), which leaves a seed cake,
   (iii) adding an aqueous solution to the seed cake and obtaining an aqueous suspension of the protein-containing residue,
   (iv) applying the aqueous suspension to an expanded bed adsorption column comprising particles having a functionalized matrix polymer with affinity to proteins in which ligands attached to the adsorbent particles provide a dynamic binding capacity of at least 20 g of protein per liter,
   (v) eluting the protein from the column of (iv), to obtain the purified protein product
   (vi) subjecting the purified protein product from step (v) to an ultrafiltration step and then returning the permeate from the ultrafiltration step back to adding step (iii) as the aqueous solution;
wherein the purified protein product comprises at the most 20% (w/w) non-protein material, the yield of the protein is at least 10 grams of protein per kg of the oil isolated in step (ii), on a dry matter basis, and wherein step (i) is performed before steps (iv) and (v).

2. The method according to claim 1, wherein the method is a continuous method of providing a biofuel and a protein product.

3. The method according to claim 1, wherein the treatment in step (i) is selected from the group consisting of extraction, grinding, milling, hacking, squeezing, slicing, abrading, pressing, crushing, chipping and any combination thereof.

4. The method according to claim 1, wherein the raw material is subjected to a further treatment resulting in a partially hydrolysed raw material.

5. A method for isolating a biofuel and a purified protein product from a raw material derived from a plant or an animal, wherein said biofuel is ethanol, said method comprising the steps of:
(i) treating the raw material to liberate a fermentable carbohydrate from the raw material and to provide a protein containing residue,
(ii) fermenting the carbohydrate liberated in step (i) to produce ethanol and isolating the ethanol,
(iii) adding an aqueous solution to the protein containing residue and obtaining an aqueous suspension of the protein-containing residue,
(iv) applying the aqueous suspension to an expanded bed adsorption column comprising particles having a functionalized matrix polymer with affinity to proteins in which ligands attached to the adsorbent particles provide a dynamic binding capacity of at least 20 g of protein per liter,
(v) eluting a protein from the column of (iv) to obtain the purified protein product,
(vi) subjecting the purified protein product from step (v) to an ultrafiltration step, and returning the permeate from the ultrafiltration step back to adding step (iii) as the aqueous solution;
wherein the purified protein product comprises at the most 20% (w/w) non-protein material and the yield of the protein is at least 10 grams of pure protein product per kg of the biofuel ethanol isolated in step (ii), on a dry matter basis, and wherein step (i) is performed before steps (iv) and (v).

6. The method according to claim 5, wherein the biofuel is separated from the fermented material by an isolation process selected from the group consisting of evaporation, extraction, distillation, centrifugation, and decanting, and any combination thereof.

7. The method according to claim 1 or 2, wherein the method further comprises a step of pH adjustment before subjecting the aqueous suspension to the expanded bed adsorption column.

8. The method according to claim 1 or 5, wherein the expanded bed adsorption process is performed at a flow-rate of at least 3 cm/min.

9. The method according to claim 1 or 5, wherein the particles having a functionalized matrix polymer with affinity to proteins further comprise a non-porous core having a density of at least 4 g/ml.

10. The method according to claim 9, wherein the particles having a functionalized matrix polymer with affinity to proteins has a mean particle size of at most 120 μm.

11. The method according to claim 1 or 5, wherein the eluting of the protein product is performed with an eluant selected from the group consisting of dilute base, dilute acid, and water.

12. The method according to claim 1 or 5, wherein the particles having a functionalized matrix polymer with affinity to proteins comprise a porous material surrounding a non-porous core, wherein said porous material comprises a polymeric base matrix.

13. The method according to claim 1 or 5, wherein the functionalized matrix polymer having an affinity to proteins comprises a plurality of covalently attached functional groups, said functional groups comprising an aromatic or heteroaromatic ring-system and/or one or more acid groups which forms a ligand or part of a ligand with affinity to proteins.

14. The method according to claim 1 or 5, wherein the eluting in the expanded bed adsorption process is performed using an eluent comprising less than 5% (v/v) of organic solvents.

* * * * *